United States Patent

Borish et al.

[11] Patent Number: 5,725,848
[45] Date of Patent: Mar. 10, 1998

[54] PERMANENT WAVING LOTION AND METHOD OF USE

[75] Inventors: Edward Borish, Mahwah, N.J.; Bridget Ijeh, Bridgeport; Thomas M. Schultz, Ridgefield, both of Conn.

[73] Assignee: Shiseido Co., Ltd., Tokyo, Japan

[21] Appl. No.: 740,850

[22] Filed: Nov. 4, 1996

Related U.S. Application Data

[63] Continuation of Ser. No. 353,510, Dec. 9, 1994, abandoned.

[51] Int. Cl.$^6$ ............................................. A61K 7/09
[52] U.S. Cl. ................................ 424/70.5; 132/211
[58] Field of Search ........................... 424/70.5; 132/211

[56] References Cited

U.S. PATENT DOCUMENTS

| | | | |
|---|---|---|---|
| 4,130,121 | 12/1978 | Wetzel | 424/70.5 |
| 4,192,863 | 3/1980 | Kondo | 424/70.5 |
| 4,548,811 | 10/1985 | Kubo et al. | 424/70.5 |
| 4,848,377 | 7/1989 | Bires et al. | 132/222 |
| 5,223,252 | 6/1993 | Kolc et al. | 132/205 |
| 5,332,570 | 7/1994 | Bergstrom et al. | 132/203 |

*Primary Examiner*—Amy Hulina
*Attorney, Agent, or Firm*—Melvin I. Stoltz

[57] ABSTRACT

A highly effective, ammonia-free, permanent waving lotion is attained by employing one a reducing agent consisting of a thiol compound or mercaptan in combination with an alkalizing agent consisting of an alkanolamine and an alkali metal hydroxide. In accordance with this invention, the reducing agent is employed either independently as an aqueous solution or in association with desired additives for imparting additional benefits to the permanently waved hair. Preferably the reducing agents of the present invention are employed in a permanent waving lotion having a pH ranging between about 5.5 and 10.0. By employing this invention, long lasting permanently waved hair is attained with substantially less malodor being produced, thereby providing increased comfort to the stylist and the person who undergoes permanent waving.

5 Claims, No Drawings

PERMANENT WAVING LOTION AND METHOD OF USE

This application is a continuation of application Ser. No. 08/353,510, filed Dec. 9, 1994 now abandoned.

TECHNICAL FIELD

This invention relates to the art of permanently waving hair, and more particularly, to new reducing agent combinations which provide substantially increased, long-lasting, durable permanently waved hair while also substantially reducing the malodor typically associated with permanent waving.

BACKGROUND ART

The permanent waving of hair is a well established and well developed art in which substantial attention has been directed to improve the present level of technology. Although substantial changes have occurred throughout the last decades, various problems continue to plague the industry in spite of numerous attempts to reduce or eliminate these problems.

In order to best understand the present state of the art and the problems existing therein, it is important to reiterate that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural biosynthesis of hair, the clement sulfur covalently links intra or inter polypeptide chains (K) through two sulfur atoms (S-S) to give keratin protein (K-S-S-K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free—SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

The most commonly used reducing agents employed in the permanent deformation of hair keratin are salts and esters of thioglycolic acid. Other less commonly used reducing agents include cysteine, cysteamine, thiolactic acid, their derivatives and mixtures thereof. These reducing agents are very effective in the reduction of disulfide bonds and under certain conditions can reduce more than 50% of the keratin cystine bonds.

Although effective in providing excellent reducing capabilities, the above mercaptans and their corresponding derivatives possess problems that are difficult to control. One of the disadvantages is the emission of malodor, which is very common with sulfur compounds. This malodor is also due to the use of an alkalizing agent, the most commonly used being ammonia. However, because of its high volatility and sharp disagreeable odor, ammonia also contributes to perm malodor. This characteristic creates discomfort to both the stylist and the individual who undergoes permanent waving. Therefore, fragrances are used with reducing agents to mask unpleasant sulfur odors. Other disadvantages include the irreversible fiber alteration as made evident by increased fiber porosity and decreased tensile properties.

Much efforts have been expended in attempts to minimize these undesirable attributes. These include pretreatments, barriers which decrease the rate of diffusion, reduction of the mercaptan concentration and/or the pH of the reducing agents, and duration of reduction time. Many of these pretreatments yield other undesirable characteristics such as oily, greasy, and dirty feeling of the hair fiber.

Furthermore, in seeking to attain an improved permanent waving lotion, numerous agents have been employed in combination with the thiol compound to provide improved results. In this regard, much effort has been expended in employing numerous compounds as the alkalizing agent used in combination with the thiol compound to control the pH level as well as to reduce the malodor associated with permanent waving. As is evident from prior art disclosures, such as found in *Handbook of Cosmetic Science*, H. W. Hibbot, Ed. The MacMillan Company, New York, N.Y. 1963, Page 393–394 and *J. Soc. Cosmet. Chem.*, Garcia et al. Volume 41, Page 149 (1990), the use of alkali metal salts has been attempted and has been found to be ineffective. As disclosed in these prior art discussions, alkali metal salts, in general, and sodium hydroxide in particular, has been found to be incapable of providing a satisfactory permanently waved head of hair when combined with a thiol compound.

As a result, the cosmetic industry has sought alternate directions for creating reducing agents which principally have focused on the use of ammonia or ammonium based compounds employed in combination with the thiol compound to produce an effective permanent wave reducing agent. However, in spite of substantial effort to attain a reducing agent which can be employed with substantially less malodor being produced, these attempts have failed to provide a composition which is capable of producing a permanently waved head of hair at least equivalent to conventional reducing lotions having these inherent deficiencies.

Furthermore, in the art of permanent waving, there is much trial and error, with the hair being over-processed, in some instances. The characteristics of over-processing are raspy feel to the hair or a loss of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical changes in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Therefore, it is a principal object of the present invention to provide a composition for permanently waving hair fibers which is capable of imparting to the head of hair a durable, long-lasting permanent hair set retention, while substantially eliminating the malodor typically resulting from the waving process.

Another object of the present invention is to provide a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition having the characteristic features described above which is capable of imparting a long-lasting permanent wave or setting property to the hair, while substantially reducing hair damage caused during the reduction and oxidation processes.

A further object of the present invention is to provide a permanent wave composition having the characteristic features described above which is capable of improving the elastic and tensile properties of the hair fibers.

Other and more specific objects will in part be obvious and will in part appear hereinafter.

DETAILED DESCRIPTION

By employing the present invention, the prior art limitations and difficulties have been overcome and a long-lasting, permanently waved head of hair is attained using a new permanent waving composition which completely eliminates the need for ammonia, resulting in a permanent wave lotion which is employed with substantially less malodor and substantially increased comfort for both the stylist and the individual whose hair is being permanently waved. In addition, the permanent waving lotion composition of the present invention provides greater control over the curl formation process, while also enhancing the physical properties of the hair fibers, such as feel, shine, luster, softness and manageability.

In accordance with the present invention, highly desirable and previously unattainable results and operating conditions are realized by employing an alkali metal hydroxide in combination with an alkanolamine as the alkalizing agent for the thiol compound. In this way, the prior art use of ammonium based compositions as the alkalizing agent for the thiol compound are eliminated.

Although the prior art has universally taught away from the use of alkali metal hydroxides as alkalizing agents with thiol compounds in permanent waving lotions, the Applicants herein have discovered that a highly effective, permanent waving lotion is established by employing an alkali metal hydroxide with an alkanolamine as the composition for adjusting the pH of a thiol compound in a permanent waving lotion. Unexpectedly and surprisingly, this unique combination produces a permanently waved head of hair with substantially less malodor than is commonly found with conventional permanent wave lotions. As a result, greater comfort is enjoyed by both the stylist and the individual whose hair is being permanently waved.

As is well known in the art of permanent waving, a thiol compound is employed in combination with an alkalizing agent in order to control the pH of the permanent waving lotion. Since the pH level of the permanent waving lotion is an important factor in determining the efficacy of the resulting wave, the pH level is tightly controlled. In addition, as discussed above, ammonium based compounds have been almost universally employed as the alkalizing agent for most permanent wave lotions. Typically, prior art alkalizing agents are selected from the group consisting of ammonia, ammonium hydroxide, ammonium carbonate, and ammonium bicarbonate. Although other agents have been employed as alkalizing agents in prior art permanent waving lotions, the ammonium based compounds have been universally adopted due to their effectiveness.

In the present invention, the need for ammonium based compounds as the alkalizing agent is completely eliminated and a new, unexpected, non-ammonium based alkalizing agent is realized, having improved performance characteristics. By employing the present invention, the pH level of the permanent waving lotion is controlled by combining the desired thiol compound with an alkalizing agent which comprises an alkali metal hydroxide in combination with an alkanolamine. Using this combination, a unique and highly effective permanent waving lotion is attained which is capable of virtually eliminating all of the principal prior art difficulties and drawbacks.

In the present invention, it has been found that the alkanolamine is preferably selected from the group consisting of monoethanolamine, diethanolamine, and triethanolamine. In addition, the preferred alkali metal hydroxide employed in combination with the alkanolamine comprises sodium hydroxide. In the present invention, the concentration of the alkanolamine preferably ranges between about 0.1% and 10% by weight of the entire weight of the permanent waving lotion, while the concentration of the alkali metal hydroxide ranges between about 0.1% and 3% by weight of the entire weight of the permanent waving lotion.

In constructing the desired permanent waving lotion of this invention, any desired thiol compound commonly employed in permanent waving can be used in combination with the alkanolamine and the alkali metal hydroxide. Preferably, the thiol compound employed is selected from the group consisting of salts and esters of thioglycolic acid.

In addition to the combination of a thiol compound or mercaptan with the alkali metal hydroxide and alkanolamine, the permanent waving lotion of the present invention also preferably incorporates additional additives which are commonly employed in permanent waving compositions. These additives impart additional benefits to the resulting permanently waved hair and include conditioning agents, fragrances, and surfactants. By employing these additional additives, the resulting permanent waving lotion provides further enhanced benefits to the resulting permanently waved hair.

In Table I, an overall general composition of a permanent wave reducing lotion made in accordance with the present invention is provided. As detailed therein, the various desired ingredients and the quantity of each ingredient are provided on a percent by weight basis, based upon the weight of the entire composition. In addition, the pH of the composition preferably ranges between about 5.5 and 10.0.

TABLE I

PERMANENT WAVE REDUCING LOTION COMPOSITION

| INGREDIENT | WEIGHT % RANGE |
|---|---|
| Alkanolamine | 0.1 to 10% |
| Alkali Metal Hydroxide | 0.1 to 3% |
| Thiol Compound | 1 to 25% |

TABLE I-continued

PERMANENT WAVE REDUCING LOTION COMPOSITION

| INGREDIENT | WEIGHT % RANGE |
|---|---|
| Surfactant | 0.1 to 4% |
| Conditioner | 0.1 to 8% |
| Fragrance | 0.1 to 3% |
| Water | q.s. to 100% |

In Table II, the preferred formulation of the present invention is provided. In this formulation, the quantity of each ingredient is provided on a percent by weight basis, based upon the weight of the entire composition. In addition, the pH of the composition is about 7.8.

TABLE II

PREFERRED PERMANENT WAVING LOTION COMPOSITION

| INGREDIENT | WEIGHT % |
|---|---|
| Monoethanolamine | 3.0 |
| Sodium Hydroxide | 0.5 |
| Glyceryl Monothioglycolate | 19.6 |
| Surfactant | 0.6 |
| Conditioner | 5.5 |
| Fragrance | 0.3 |
| Water | q.s. to 100% |

In employing the present invention, a generally conventional application process is employed. In this regard, the permanent wave reducing lotion detailed above can be employed or, if desired, an aqueous solution of the thiol compound, the alkali metal hydroxide and the alkanolamine can be employed. Regardless of which composition is used, the same generally conventional application process is followed.

In this application process, the pH adjusted reducing agent or the permanent wave reducing lotion is applied directly to freshly shampooed and moistened hair which has been previously rolled on rollers. The hair fibers are thoroughly wetted by the reducing agent or the permanent wave reducing lotion, which is then allowed to remain on the moistened hair for between about ten and sixty minutes. Although this range has been found to be effective, the reducing agent or lotion is preferably allowed to remain on the hair for between about five and thirty minutes. If desired, the reaction may be accelerated by applying heat to the hair. However, it has been found that heat is not usually required.

Once the desired reaction time has been achieved, the hair is rinsed with water and blotted to remove excess moisture. Then, the hair is neutralized or oxidized with a solution which incorporates one or more agents selected from the group consisting of acidic hydrogen peroxide, alkaline bromate, and sodium chlorite. Preferably, the oxidizing solution is applied to the hair and allowed to remain on the hair for between about two and ten minutes. However, alternate time ranges can be employed without departing from the scope of this invention. Finally, the hair tresses are rinsed with running water for two minutes, unwound from the rod, and allowed to dry.

By employing the present invention, a substantially improved and enhanced permanently waved head of hair is attained. Furthermore, the reduction process is achieved with substantially less malodor being produced, thereby increasing the comfort of the application process for both the stylist and the recipient. In addition, the present invention imparts physical characteristics to the resulting permanently waved hair, such as gloss, combability and softness, while also substantially increasing curl retention and hair set permanency. As a result, the present invention is capable of eliminating most of the prior art problems, while providing a highly effective reducing agent for permanently waving heads of hair in a more comfortable manner than is presently attained with state of the art formulations.

The invention accordingly comprises the several steps and relation of one or more such steps with respect to each of the others and the composition possessing the features, properties and relation of components all as exemplified herein with the scope of the invention being indicated in the claims.

BEST MODE FOR CARRYING OUT THE INVENTION

The following examples are provided in order to substantiate the efficacy of the reducing agent created by combining a mercaptan or thiol compound with an alkalizing agent consisting of an alkali metal salt and an alkanolamine. This efficacy is shown herein, along with the ability of the composition of the present invention to permanently wave hair with substantially improved, long-lasting physical enhancements and characteristics being realized. However, it is to be understood that the following examples are intended as a teaching of the best mode for carrying out the present invention and are not intended to limit the breadth of this discovery.

As is evident from a review of the following examples, the present invention is centered upon the discovery that a unique reducing composition is realized by combining a mercaptan or thiol compound with an alkalizing agent consisting of an alkali metal hydroxide in combination with an alkanolamine. The reducing agent achieved provides substantially enhanced benefits and results.

In order to demonstrate these enhanced benefits and the efficacy of the present invention, numerous hair tresses were tested by being permanently waved using the compounds of the present invention as the reducing agent and comparing these results to hair tresses permanently waved with conventional prior art reducing agents. In order to provide a standard by which the waving efficiency of the reducing agents can be objectively evaluated, the "Deficiency in Wave Tightness" (DIWT) was determined for each sample and compared.

In determining the Deficiency in Wave Tightness (DIWT), the Test Tube Test Curl (TTTC) procedure was used for each reducing agent. Using this procedure, twelve freshly shampooed, normal human hair fibers were knotted at the root end and cut to a length of 3.5 inches from the knot. The bundle was immersed in water and then wound around a glass mandrel having a diameter of 7.0 mm. Thereafter, the bundle and mandrel were immersed into 15 ml of the reducing solution at a constant temperature of about 32° C., and allowed to remain for 10 minutes. Once completed, the hair fibers were rinsed with running water for two minutes.

After rinsing, the hair fibers were immersed in 15 ml of the neutralizer and allowed to stand for five minutes. Then, the hair fibers were rinsed with running water for two minutes. Following the rinsing, the hair fibers were unwound from the aluminum mandrel and the obtained coil was immersed in water. Thereafter, the diameter of the resulting hair coil was recorded.

Using this data, the Deficiency in Wave Tightness (DIWT) was determined, which represents the overall waving efficiency of the reducing agent. In general, acceptable DIWT results range between about 8 and 60.00. The "Deficiency in Wave Tightness" or DIWT is calculated as follows:

$$DIWT = \frac{\text{diameter of hair coil (mm)} - \text{diameter of mandrel (mm)}}{\text{diameter of mandrel (mm)}} \times 100$$

EXAMPLES

In order to demonstrate the efficacy of a permanent wave lotion which incorporates a thiol compound and an alkalizing agent consisting essentially of an alkanolamine and an alkali metal hydroxide, numerous tests were conducted on various types of hair fibers using both the present invention and a conventional ammonium based prior art permanent wave lotion using the glyceryl ester of thioglycolic acid.

In Table III, the results obtained from these tests are detailed. As shown in Table III, numerous tests were conducted using identical procedures on normal, virgin hair fibers, colored or dyed hair fibers, which have received previous permanent wave treatments, and bleached hair fibers. In each instance, numerous tests were conducted on a plurality of samples for each hair type and for each permanent wave lotion and the resulting Deficiency In Wave Tightness was determined. In Table III, the overall average attained for the Deficiency In Wave Tightness for each hair type is provided for both the permanent wave lotion of Table II as well as the prior art permanent wave lotion.

TABLE III

DIWT RESULTS FOR PRIOR ART WAVE LOTION AND PREFERRED WAVE LOTION

| | Deficiency in Wave Tightness | |
|---|---|---|
| Hair Type | Wave Lotion of Table II | Ammonia Based Permanent Wave Lotion |
| Normal | 38.10 ± 1.21 | 33.95 ± 4.02 |
| Color treated | 59.71 ± 0.73 | 36.72 ± 1.93 |
| Bleached | 35.24 ± 4.30 | 30.48 ± 1.78 |

By comparing the results provided in Table III, it is evident that the use of the composition of the present invention produced permanently waved hair fibers which are virtually identical to the results attained by employing prior art conventional ammonium based permanent wave lotions. In addition, it was found that substantially less malodor was produced when the composition of Table II was employed as compared to the conventional prior art ammonium based permanent wave lotion.

It will thus be seen that the objects set forth above, among those made apparent from the preceding description, are efficiently attained and, since certain changes may be made in carrying out the above process and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in the claims, ingredients or compounds recited in the singular are intended to include compatible mixtures of such ingredients wherever the sense permits.

Having described our invention, what we claim as new and desire to secure by Letters Patent is:

1. A process for providing enhanced permanent waving of hair with substantially less malodor being produced, said process consisting of the following steps
   A. forming a permanent waving lotion consisting of:
      a. between about 1% and 25% by weight of the total composition of one thiol compound selected from the group consisting of salts and esters of thioglycolic acid,
      b. an alkalizing agent consisting of
         1. between about 0.1% and 10% by weight of the total composition of an alkanolamine, and
         2. between about 0.1% and 3% by weight of the total composition of an alkali metal hydroxide,
      c. between about 0.1% and 4% by weight of the total composition of a surfactant,
      c. between about 0.1% and 8% by weight of the total composition of a conditioning agent,
      d. between about 0.1% and 3% by weight of the total composition of a fragrance, and
      e. water forming the balance;
   B. moistening hair to be permanently waved;
   C. rolling the moistened hair fibers onto curlers for securement thereto;
   D. applying the permanent waving lotion to the rolled hair fibers;
   E. allowing the permanent waving lotion to remain on the hair for between about 10 and 60 minutes;
   F. rinsing the hair with water and blotting to remove excess moisture; and
   G. neutralizing or oxidizing the hair by employing a solution comprising one or more agents selected from the group consisting of acidic hydrogen peroxide, bromate, and sodium chlorite.

2. A process for providing enhanced permanent waving of hair with substantially less malodor being produced, said process consisting of the following steps
   A. forming a permanent waving lotion consisting of
      a. between about 1% and 25% by weight of the total composition of one thiol compound selected from the group consisting of salts and esters of thioglycolic acid,
      b. an alkalizing agent consisting of
         1. between about 0.1% and 10% by weight of the total composition of an alkanolamine, and
         2. between about 0.1% and 3% by weight of the total composition of an alkali metal hydroxide.
      c. between about 0.1% and 4% by weight of the total composition of a surfactant,
      c. between about 0.1% and 8% by weight of the total composition of a conditioning agent.
      d. between about 0.1% and 3% by weight of the total composition of a fragrance, and
      e. water forming the balance;
   B. moistening hair to be permanently waved;
   C. rolling the moistened hair fibers onto curlers for securement thereto;
   D. applying the permanent waving lotion to the rolled hair fibers;
   E. allowing the permanent waving lotion to remain on the hair for between about 10 and 60 minutes;
   F. rinsing the hair with water and blotting to remove excess moisture; and
   G. neutralizing or oxidizing the hair by employing a solution comprising one or more agents selected from the group consisting of acidic hydrogen peroxide, bromate, and sodium chlorite; and
   H. heating the hair during the processing of the permanent waving lotion.

3. The process defined in claim 2, wherein said hair is further defined being heated to a temperature of about 50° C.

4. The process defined in claim 1, wherein the permanent waving lotion is further defined as being prepared by intermixing all of the components therefor except the thiol compound and intermixing the thiol compound with the previously prepared additives immediately prior to applying the permanent waving lotion to the head of hair to be permanently waved.

5. The process defined in claim 4, wherein the permanent waving lotion is further defined as being prepared by separately intermixing the thiol compound with the alkalizing agent, with said alkalizing agent having a quantity sufficient to enable the pH level of the permanent waving lotion to range between about 5.5 and 10.0.

* * * * *